(12) United States Patent
Lu

(10) Patent No.: US 6,709,683 B2
(45) Date of Patent: Mar. 23, 2004

(54) METHOD FOR PRODUCING COMPOSITION OF FERMENTED ASTRAGALUS (HUANG QI) FOR INHIBITING THE GROWTH OF BACTERIA

(75) Inventor: Kung-Ming Lu, Taipei (TW)

(73) Assignee: Micorbio Co., Ltd., Taipei (TW)

( * ) Notice: Subject to any disclaimer, the term of this patent is extended or adjusted under 35 U.S.C. 154(b) by 0 days.

(21) Appl. No.: 10/219,308

(22) Filed: Aug. 16, 2002

(65) Prior Publication Data

US 2004/0033278 A1 Feb. 19, 2004

(51) Int. Cl.[7] ................................................. A61K 35/78
(52) U.S. Cl. ........................ 424/757; 424/725; 424/115
(58) Field of Search ................................. 424/757, 725, 424/115

(56) References Cited

PUBLICATIONS

Derwent English abstract of CN 118799 A (1998).*
Derwent English abstract of CN 1271001 A (2000).*

* cited by examiner

*Primary Examiner*—Francisco Prats
*Assistant Examiner*—Susan D Coe
(74) *Attorney, Agent, or Firm*—Rosenberg, Klein & Lee

(57) ABSTRACT

This invention relates to a method of producing fermented extract to obtain composition that has inhibition action on bacteria infection. The fermented extract is prepared by symbiotic culture of yeast and lactic acid bacteria, removing microbial cells from the resultant culture solution and concentrating the prepared culture solution.

5 Claims, No Drawings

METHOD FOR PRODUCING COMPOSITION OF FERMENTED ASTRAGALUS (HUANG QI) FOR INHIBITING THE GROWTH OF BACTERIA

BACKGROUND OF THE INVENTION

1. Field of Invention

The present invention relates to the preparation of therapeutic compositions comprising fermented extracts. The fermented extract is prepared by fermenting an aqueous astragalus (Huang Qi) together with at least one lactic acid bacteria and a yeast; or by fermenting an aqueous astragalus extract and *Glycine max* (L.) extract (such as soybean and black soybean) together with at least one lactic acid bacteria and a yeast. The invention also relates to therapeutic uses of such extracts in the treatment, prophylaxis, amelioration of, or defense against a variety of bacteria growth.

2. Description of the Prior Art

For many thousands of years, astragalus (Huang Qi) has been used by traditional Chinese practitioners as an herbal tonic for strengthening the body. It is officially listed in the Chinese Pharmacopoeia and used mainly as a tonic and for the treatment of nephritis and diabetes. Analysis of astragalus has revealed some of the following components that are responsible for its active effects: polysaccharides, monosaccharides, flavonoid, alkaloid, including choline and betaine, folio acid, various amino acids, mucoitin, gum, cellulose, picrorhiza, and fourteen mineral trace elements, including selenium, zinc, iron, etc.

This is better known to us astragalus can provide a powerful stimulus to the immune system. In the United States, astragalus has been presented as an immune stimulant useful for treating colds and flues. Many people have come to believe that they should take astragalus, like echinacea, at the first sign of a cold. Astragalus now is assured a place in Western herbal healing.

The belief that astragalus can strengthen the immunity has its basis in Chinese tradition. The expression "stabilize the exterior" means helping to create a "defensive shield" against infection. Normally astragalus will boost the immune system over long periods of time; therefore it is often used to modulate the immune system in the long-term recovery of people with moderate to severely weakened immune systems.

Numerous scientific studies have confirmed the medicinal value of astragalus. Studies have confirmed that it contains medicinally active compounds, including a polysaccharide that stimulates the immune system. Research has also shown that subjects with advanced cancer showed a two to three fold increase in the strength of their immune response after being given astragalus. Pharmacological studies in the West confirm that astragalus increase the activity of several kinds of white blood cells as well as production of antibodies and interferon. These attributes make it suitable for use as a preventative against recurring colds, flu and bronchitis, as well as an adjunct to treating chronic illnesses and supporting long-term recovery from debilitating viral infections.

Astragalus is available in many forms. Chinese drug store sell dry roots, some stores sell powder of the roots, some market the extract, while others make it the central ingredient of herbal teas. However, none of the market line products are prepared through fermentation and are used in the treatment, prophylaxis, amelioration of, or defense against a variety of bacteria growth. Present invention substitutes the unique symbiotic fermentation with beneficial microorganisms for traditional extractions to efficiently extract potent components from astragalus or the combination of astragalus and *Glycine max* (L.). This preparation process not only increases pharmacology activities, but also makes the fermented extracts beneficial in defense against a variety of bacteria infections. From our preparation, the composition becomes a most unique and has a potential use for the prevention and treatment of infection. Therefore, present fermentation process can be considered to be one of the most promising manufacture processes.

SUMMARY OF THE INVENTION

In its broadest aspect this invention is concerned with a composition comprising a fermented astragalus extract or fermented astragalus and *Glycine max* (L.) extract, which is manufactured by the co-cultivation of a yeast and lactic acid bacteria. Particularly, *Glycine max* (L.) is soybean or black soybean. More particularly, the fermented extract of the invention include the fermented astragalus extract, fermented extract of astragalus and soybean, and fermented extract of astragalus and black soybeans Such compositions may be in the form of pharmaceutical compositions, in association with one or more pharmaceutically acceptable carriers, excipients, auxiliaries and/or diluents.

In another aspect this invention is to provide a method for inhibiting bacteria growth in a subject comprising administering an effective amount of a fermented astragalus extract or comprising administering an effective amount of a fermented astragalus and *Glycine max* (L.) extract, wherein the fermented extract is prepared by the co-cultivation of a yeast and lactic acid. In particular, the fermented extract of the invention has potent anti-infection activity thereby allowing for prophylaxis, amelioration, prevention and/or treatment of microbial infection and promoting health.

In accordance with another aspect of this invention there is provided a process for the production of a composition comprising a fermented astragalus extract or together with *Glycine max.* (L.), which is manufactured by the co-cultivation of a yeast and lactic acid bacteria. Particularly, *Glycine max* (L.) is soybean or black. More particularly, the fermented extracts of the invention include the fermented astragalus extract, fermented extract of astragalus and soybean and fermented extract of astragalus and black soybean.

DETAILED DESCRIPTION OF THE PREFERRED EMBODIMENTS

Process for Producing the Fermentation Product:

The fermented composition is obtained from the filtrate of the culture medium obtained by carrying out co-cultivation of two or more sorts of useful bacilli chosen from a yeast and lactic acid bacteria in a specific combination by condensing method.

According to the invention, the preferred *Glycine max* (L.) used in the preparation of the fermented extract is selected from the group consisting of soybean and black soybean. More particularly, the fermented extracts of the invention include the fermented astragals extract, fermented extract of astragals and soybean and fermented extract of astragals and black soybean.

The composition of the invention is produced by fermentation of astragals with or without combination of *Glysine max* (L.) in the presence of useful bacilli chosen from a yeast and lactic acid bacteria. The fermentation is carried out co cultivation of two or more sorts of yeast and bacteria strains, e.g. one or more strains of a Lactobacillus species or several strains of a number of Lactobacillus species, together with at lest one yeast, e.g. one or more strains of a Saccharomyces species or several strains of a number of Saccharomyces species. The fermentation process can be carried out sequentially in any order or simultaneously, preferably simultaneously.

If more than one microbe is used in the fermentation, the fermentation can be conducted with the microbe sequentially or simultaneously. Preferably, the fermentation is carried out using a heterogeneous culture of Lactobacillus, for example, a culture of 2,4,6,8 or 10 strains of Lactobacillus and at least one yeast is added to the heterogeneous culture of Lactobacillus. The strains of Lactobacillus that can be used include, for examples, *Lactobacillus acidophilus* CCRC 10695, 14026, 14064, 14065 and/or 14079, *Lactobacillus sp*: CCRC 14044, 14061, 14631, and/or 16000, *Lactobacillus delbruecki bulgaricus* CCRC 10696, 14007, 14009, 14010, 14069, 14071, 14098, *Lactobacillus delbrueckiibulgaricus* CCRC 10696; 14007, 14009, 14010, 14069, 14071, 14098 and/or 16054, *Streptococcus thermophilus* CCRC 11080, 12308, 13869, 14085 and/or 14089, and/or *Bifidobacterium longum* CCRC 11847, 13869, 14605 and/or 14634. The yeast that can be used include, for example, *Saccharomyces cerevisiae* CCRC 20577, 20578, 20581, 21494, 21550, 21680, 21805, 22138, 22234, 22337, 22731 and/or 22728, and/or *Candida kefyr* CCRC 21269, 21742 and/or 22057. After fermentation, the fermented liquid is filtered and centrifuged to remove most or all of the dead microbe to obtain the pure fermented extract. More preferably, the filtration step is followed by removal of some of the water from the filtrate to concentrate the fermented liquid to obtain the final fermented extract.

The process is carried out by first preparing a special culture medium. Various bacteria and yeast strains are transferred to the special medium and placed in an incubator set at 37–42 degrees centigrade for 18–36 hours to obtain bacteria both. Boil astragalus flakes in distilled water for 60 minutes and then filter to obtain the astragalus extract. More perfectly, mix astragalus extract with *Glysine max* (L.) powder in distilled water. Boil at 121 degrees centigrade for 20 minutes and then filtrate to obtain astragalus and *Glysine max* (L.) extract. The bacteria broth is added to astragalus and *Glysine max* (L.) extract and cocultivate at 36–42 degrees centigrade for 42–60 hours. Upon completion of the incubation period, the fermented liquid is filtered and heat sterilized; and 93–96% of the water content of the filtrate is removed to obtain a final fermented extract.

Use of the fermented composition:

Use as an antimicrobial agent to prevent or treat infections:

The fermented extract has demonstrated antimicrobial activity in vitro. It inhibits the growth of *Pseudomonas aeruginosa, Klebsiella pneumoniae* and Methicillin resistant *Staphylococcus aureus*.

This invention will now be described with reference to the following non-limiting examples.

EXAMPLE 1

An example of the manufacture process of this composition concerning this invention is given as below. The process comprises the following steps:

1. Step 1 (Preparation of a Special Culture Medium):

Dissolve yeast extract and lactose in distilled water. Autoclave for sterilization. A culture medium is prepared.

2. Step 2 (Pure Culture of a Useful Bacteria Strains)

Various kinds of bacteria and yeast strains are transferred to the special culture medium prepared at the step 1 process. Cultivate at 37–42 degrees centigrade for 24 hours.

3. Step 3 (Preparation of a Astragalus Culture Medium)

Boil astragalus flakes in distilled water at 100 degrees centigrade and then filtered to obtain the astragalus extract.

4. Step 4 (Preparation of a Special Culture Medium for Fermentation):

Mix astragalus medium obtained in step 3 with or without black soybean or soybean powder and sugar in distilled water in a flask. Autoclave at 121 degrees for sterilization. A special culture medium is manufactured.

5. Step 5 (Co-cultivation of a useful Bacteria Strains)

The useful bacteria culture at step 2 is transferred onto the special culture medium prepared in the process of step 4. Cultivate at 36–42 degrees centigrade for 42–60 hours.

6. Step 6 (a Halt and Concentration of Cultivation):

Upon completion of the incubation period, the fermented extract manufactured in the process at step 5 is filtered and centrifuged to obtain a supernatant. The supernatant solution is condensed to about 1/15 (93–96% of moisture is removed).

7. Step 7 (Final Fermentation Product):

The product obtained according to the process is enclosed with a container, and it considers as a concentrated fermentation product through legal heating. The final product has a PH at 3.2–3,5.

EXAMPLE 2

The anti-microbial activity of the fermented extract was demonstrated by determining with in vitro method.

In this experiment, the minimal inhibitory concentration (MICs) of the fermented extract was determined in *Pseudomonas aeruginosa, Klebsiella pneumoniae* and Methicillin resistant *Staphylococcus aureus*. Suspensions of these bacteria were adjusted to $3\times10^5$ CFU/ml. The adjusted bacteria suspensions were added to a 96-well plate with or without various concentration of the fermented extract. The plate was then incubated at 37° C. for 18–22 hours. The MIC from which growth was prevented was measured incubation and shown in below Table 1.

TABLE 1

| Microbe Extract (%) | *Pseudomonas aeruginosa* | *Klebsiella pneumoniae* | Methicillin resistant *Staphylococcus aureus* |
|---|---|---|---|
| Astragalus | 0.78 | 0.78 | 0.0975 |
| Astragalus + Soybean | 0.78 | 0.78 | 0.0975 |
| Astragalus + Black soybean | 0.78 | 0.78 | 0.0975 |

What is claimed is:

1. A method for producing a composition of fermented astragalus for inhibiting the growth of bacteria, comprising the following steps:

a. preparing a first culture medium by dissolving yeast extract and lactose in distilled water;

b. inoculating at least one strain of bacteria and at least one strain of yeast into the first culture medium prepared in step (a), the inoculated first culture medium being incubated at 37–42 degrees centigrade for 24 hours;

c. preparing an astragalus extract by mixing Astragalus flakes in distilled water and boiling the mixture, the boiled mixture subsequently being filtered to obtain the astragulus extract;

d. preparing a second culture medium by mixing the astragalus extract with *Glycine max* (*L.*) powder and sugar in distilled water, the second culture medium being sterilized in an autocalve;

e. combining the inoculated first culture medium with the second culture medium and incubating the combination at 36–42 degrees centigrade for 42–60 hours;

f. filtering and centrifuging the incubated combination of step (e) to obtain a supernatant solution, the supernatant solution being condensed to remove 93–96% of moisture thereof; and g. packaging the condensed supernatant solution to provide a concentrated fermentation product.

2. The method for producing a composition of fermented astragalus for inhibiting the growth of bacteria as claimed in claim 1, wherein step (b) is carried out by co-cultivation of at least two strains of lactic acid bacteria.

3. The method for producing a composition of fermented astragalus for inhibiting the growth of bacteria as claimed in claim 2, wherein the lactic acid bacteria is a Lactobacillus species.

4. The method for producing a composition of fermented astragalus for inhibiting the growth of bacteria as claimed in claim 1, wherein the at least one strain of yeast is a Saccharomyces species.

5. The method for producing a composition of fermented astragalus for inhibiting the growth of bacteria as claimed in claim 1, wherein the composition has a pH between 3.2–3.5.

* * * * *